US012337915B2

(12) United States Patent
Okafor (10) Patent No.: US 12,337,915 B2
(45) Date of Patent: Jun. 24, 2025

(54) UNIVERSAL DOCKING BRACKET

(71) Applicant: Chukwudi Joel Spencer Okafor, London (GB)

(72) Inventor: Chukwudi Joel Spencer Okafor, London (GB)

(*) Notice: Subject to any disclaimer, the term of this patent is extended or adjusted under 35 U.S.C. 154(b) by 0 days.

(21) Appl. No.: 17/669,996

(22) Filed: Feb. 11, 2022

(65) Prior Publication Data

US 2022/0185406 A1    Jun. 16, 2022

Related U.S. Application Data

(60) Provisional application No. 63/125,990, filed on Dec. 16, 2020.

(51) Int. Cl.
*B62H 3/12*     (2006.01)
*A61L 2/10*     (2006.01)
*B62H 3/08*     (2006.01)

(52) U.S. Cl.
CPC .................. *B62H 3/12* (2013.01); *A61L 2/10* (2013.01); *B62H 3/08* (2013.01)

(58) Field of Classification Search
CPC ............... B62H 3/12; B62H 3/08; A61L 2/10
See application file for complete search history.

(56) References Cited

U.S. PATENT DOCUMENTS

| | | | | |
|---|---|---|---|---|
| 4,015,718 A | * | 4/1977 | Bernard | B62H 3/08 211/20 |
| 5,492,228 A | * | 2/1996 | Botkin | B62H 3/12 211/205 |
| 5,845,788 A | * | 12/1998 | Robolin | B62H 3/00 211/121 |

(Continued)

FOREIGN PATENT DOCUMENTS

| | | | | |
|---|---|---|---|---|
| CN | 108060806 B | * | 11/2019 | ............. E04H 6/005 |
| CN | 209719785 U | * | 12/2019 | ............... B62H 3/08 |

(Continued)

OTHER PUBLICATIONS

Omniflow Omiled and Omnibench product page https://www.omniflow.io/mobility webarchive.org dated: Sep. 28, 2020 (Year: 2020).*

(Continued)

*Primary Examiner* — Terrell L McKinnon
*Assistant Examiner* — Ding Y Tan (57) ABSTRACT

In an embodiment, a universal docking bracket system for vehicles is provided. The system comprises a two-level charging and docking station comprising an upper-level port and a lower-level port. Each port comprises a cradle that supports a front wheel of a two-wheeled vehicle, a locking module that grips a center of the vehicle, and an indentation for placement of a rear wheel of the vehicle. The vehicle is a plug-in Personal light electric vehicle comprising an electric scooter. The vehicle is folded flat prior to docking by the system. Each port further comprises a retractable charging cable that connects to the vehicle and recharges a battery in the vehicle. The vehicle while docked and receiving charging is positioned vertically and in an upside-down manner on either port. The locking module has an electronically powered retractable bar that locks a footrest/base of the vehicle against the port.

12 Claims, 10 Drawing Sheets

(56) References Cited

U.S. PATENT DOCUMENTS

| | | | | |
|---|---|---|---|---|
| 6,637,602 | B2 * | 10/2003 | Dueck | A47F 7/00 |
| | | | | 211/17 |
| 7,946,432 | B1 * | 5/2011 | Swanson | B62H 3/08 |
| | | | | 211/20 |
| 2019/0263281 | A1 * | 8/2019 | Wang | B60L 53/60 |
| 2020/0031247 | A1 * | 1/2020 | Moravick | B60L 50/20 |
| 2021/0046835 | A1 * | 2/2021 | North | B60L 53/30 |
| 2021/0178921 | A1 * | 6/2021 | French | B60L 53/31 |
| 2021/0300491 | A1 * | 9/2021 | Carracelas | B62M 6/90 |
| 2022/0080847 | A1 * | 3/2022 | Allison | B60L 53/16 |

FOREIGN PATENT DOCUMENTS

| | | | | |
|---|---|---|---|---|
| KR | 20120024055 A * | 3/2012 | | |
| WO | WO-2021095024 A1 * | 5/2021 | | B62H 3/04 |
| WO | WO-2021191087 A1 * | 9/2021 | | B62H 3/04 |
| WO | WO-2021224647 A2 * | 11/2021 | | B60L 5/005 |

OTHER PUBLICATIONS

Lumistrips online product page for Nichia UV-LED for disinfection of virus and bacteria, webarchive.org dated at Nov. 27, 2020 (Year: 2020).*

Cailey Rizzo article for Honeywell UV cabin system for robotic UV disinfectant machine tested by JetBlue airline, published on Jul. 30, 2020 (Year: 2020).*

Falco UK ltd youtube video dated Mar. 18, 2020 titled "FalcoLevel premium+ two tier cycle rack" https://www.youtube.com/watch?v=Ka0kFIWyXIM (Year: 2020).*

Ground control system facebook page dated Sep. 27, 2018 titled "The 3-points of contact for bicycle security" https://www.facebook.com/groundcontrolsystems/videos/the-3-point-of-contact-for-bicycle-security/264824900834123/ (Year: 2018).*

* cited by examiner

UNIVERSAL DOCKING BRACKET

CROSS REFERENCE TO RELATED APPLICATIONS

The present disclosure is related to U.S. Provisional Patent Applicant No. 63/125,990 filed Dec. 16, 2020, the contents of which are incorporated herein in their entirety.

FIELD OF THE DISCLOSURE

The present disclosure is in the field of parking and storage of vehicles. More particularly, the present disclosure provides multiple level universal docking bracket systems for storing and recharging Personal light electric vehicles (including Electric PLEV's) that efficiently use floor space.

BACKGROUND

Electric vehicle technology is advancing rapidly. As a result, Personal light electric vehicles or PLEV's are becoming particularly popular for the urban inner city traveler, conscious of their carbon footprint and determined to find realistically achievable ways they can reduce their carbon emissions. Improved battery technology and electric motor capabilities are also contributing to this development.

Personal light electric scooters are an improvement on the traditional "two-wheeled kick scooter" that has gained widespread use in cities and urban environments. Personal light electric scooters take the shape, frame, and design of the traditional kick scooters and attach a rechargeable battery with an electric motor that drives the rear wheel. Benefits of Personal light electric vehicles include:

- PLEV's are compact and fold flat based on a hinge/pivot at the base of the handlebars.
- PLEV's are convenient and have become popular for commuting or leisure activities in cities.
- PLEV's are clean and require no fossil fuels such as gasoline.
- PLEV's are lighter than fuel-powered PLV's.
- PLEV's may be taken on public transport, such as trains and buses.
- PLEV's are easy to master and require very little practice to ride safely.
- PLEV's are a convenient, clean, and low-cost means of transport.

As Personal light electric vehicles increase in popularity, storage of PLEV's at busy locations may present challenges. Workplaces, health clubs, co-working spaces, schools, and government buildings may all eventually face this problem. As more and more Personal light electric vehicles are utilized due to the many benefits, finding space to store and charge the vehicles may become difficult.

Current PLEV docking solutions service small vehicle quantities and are not efficient enough to handle higher numbers of vehicles without consuming large amounts of floor space. In cities and urban environments, floor space is expensive and in short supply. Inefficient storage methods may lead to businesses, schools, hospitals, residential buildings, and government buildings declining to store PLEVs, whereas this convenient and environmentally friendly form of transport is favored by many and presents one of the few broadly accessible forms of clean mobility. Therefore, a need exists for a more environmentally friendly and efficient charging and docking storage solution for Personal light electric vehicles.

DETAILED DESCRIPTION

Systems and methods described herein provide a universal docking bracket comprising a multiple level charging and docking station for Personal light electric vehicles (PLEVs). In an embodiment, the system has two levels of storage space, one lower level and one upper level.

A Personal light electric vehicle is first folded flat before being mounted into the docking station port for storage. The Personal light electric vehicle has four points of contact with the docking station port while it is stored. The first is a cradle that supports the front wheel of the PLEV. The second is a locking module that grips the center of the PLEV. The locking module has an electronically powered retractable bar that locks a footrest/base of the PLEV against the docking stations port, securing the PLEV in place.

The third point of contact is an indent that the rear wheel sits within. The fourth is a retractable charging cable that connects to the Personal light electric vehicle and recharges the battery.

The lower-level storage port is readily accessible and does not need to be moved for a user to mount a PLEV within it. The upper-level port can be lowered for a user to gain access to it and mount a PLEV on the upper-level port. Once the PLEV is mounted within the upper-level port, the level can then be raised with assistance back to its higher position, reducing the amount of floor space required to store multiple PLEV's.

The upper-level storage port is moved and lowered via electrically powered linear and pneumatic actuators. When in a stored position the port is at an approximate angle of 30 degrees to the vertical. The first step in lowering the port from a stored position to ground level, for mounting or dismounting a PLEV, is to move the port to a vertical position. This is achieved with a horizontal linear actuator that extends from the casing and rotates the port.

In a second step, the port is lowered via telescopic guides and pneumatic actuators. This action places the upper-level storage port at ground level for easy access to mount or dismount a PLEV. Once finished the user can then raise the PLEV using the same process in reverse, storing the PLEV above the lower level. This storage arrangement of PLEVs may increase the efficiency of the docking station relative to the floor space required.

Several structures of docking stations are provided herein that may be deployed depending on requirements of the environment in which they are to be installed. A first structure is a rotating circular frame that may be attached to a ground or floor surface or suspended from a ceiling. This structure may be suitable when the docking station is to be installed in an open space away from a wall. In this orientation, the docking may support eight PLEVs on an upper level and four PLEVs on the lower level.

A second structure is a wall mounted docking station. This orientation typically supports one PLEV on the upper level and one PLEV on the lower level. Multiple docking stations may be mounted side by side along a wall.

Systems and methods incorporate a retractable universal fast charging cable that protrudes from each of the device's stem ports, at both the lower level and upper level. The retractable cable port is built into a side of the locking case. The system is powered by three phase mains power and may connect to existing smart grid technology.

A light strip is built into the system and is installed vertically from the base to the top of the structure. It contains UVEDs (Ultraviolet Emitting Diodes) which operate at varying nm wavelengths. The Ultraviolet light kills germs and sterilizes Personal light electric vehicles mounted within.

Figure 1:
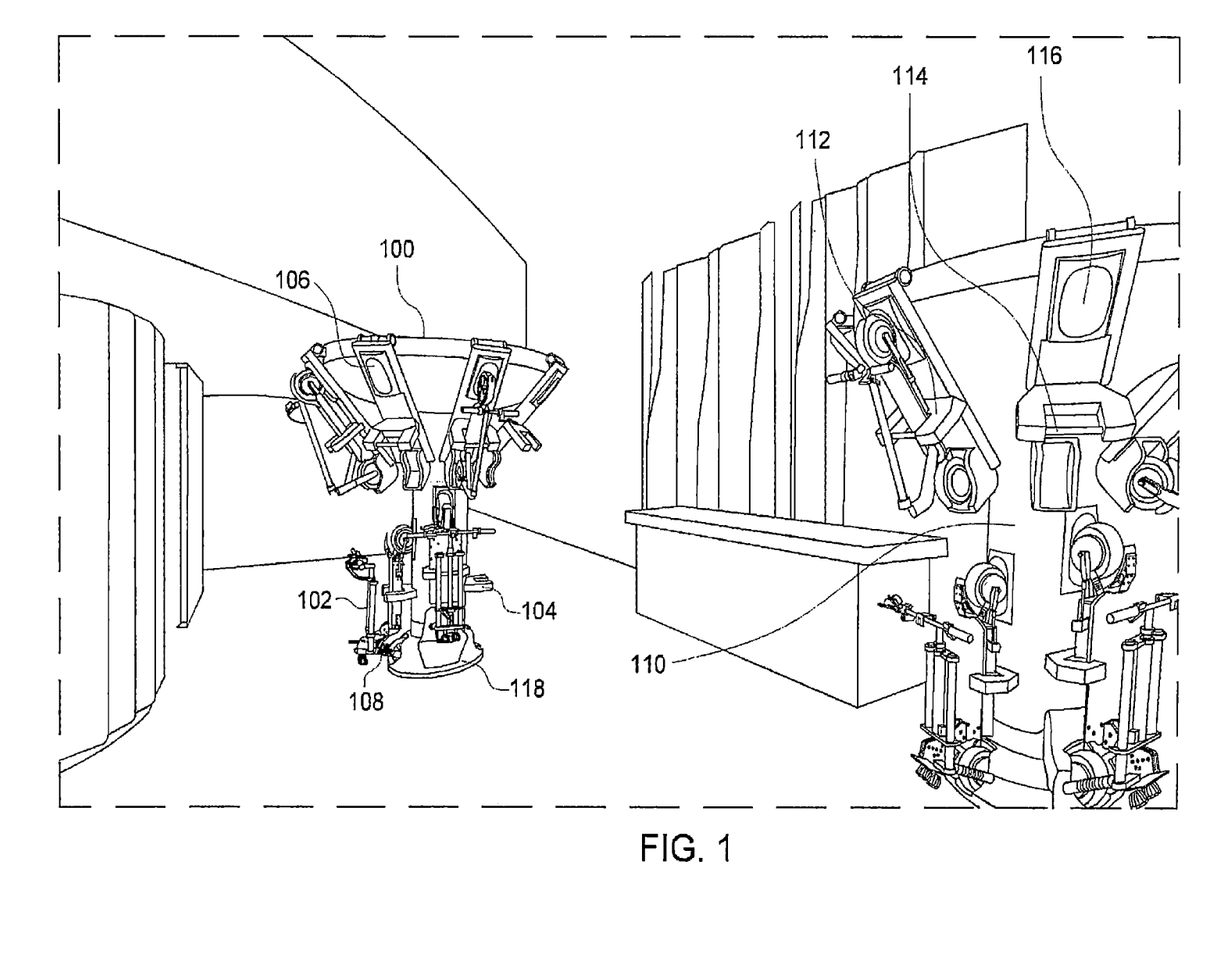
FIG. 1 is an illustrative representation of the universal docking bracket depicting a rotating circular frame orientation in accordance with an embodiment of the present disclosure.

Turning to the figures, FIG. 1 is an illustrative representation of the universal docking bracket provided herein depicting the rotating circular frame orientation in accordance with embodiments of the present disclosure. The system provides a charging and docking station 100 for Personal light electric vehicles (PLEVs) 102. The system has two levels of storage space, one lower level 104, and one upper level 106. A Personal light electric vehicle is first folded flat 108 before being mounted into the docking station 100 for storage.

The PLEV has four points of contact with the docking station 100 while it is stored. The first is a cradle 110 that supports the front wheel of the PLEV. The second is a locking module 112 that grips the center of the PLEV. The locking module 112 has an electronically powered retractable bar 114 that locks the footrest/base of the PLEV against the docking station 100, securing the PLEV in place. The third point of contact is an indent 116 that the rear wheel sits within. The fourth is a retractable charging cable that connects to the PLEV and recharges the battery.

The lower-level storage port is readily accessible and does not need to move for a user to mount a PLEV within it. The upper-level storage port can be lowered for a user to gain access to it and mount a PLEV within. Once the PLEV is mounted within the port, the PLEV and the upper-level storage port in its temporarily lowered state can then be raised back to its higher position. Storing PLEVs at more than one level reduces the amount of floor space required to store multiple PLEVs.

Several orientations of docking stations 100 may be deployed depending on the requirements of the environment they are to be installed in. In the embodiment illustrated in FIG. 1, a rotating circular frame can be attached to the ground 118 or suspended from a ceiling. The circular frame may be suitable when the docking station is to be installed in an open space away from a wall. The rotating circular frame may support eight PLEVs on an upper level and four PLEV's on a lower level.

Figure 2:
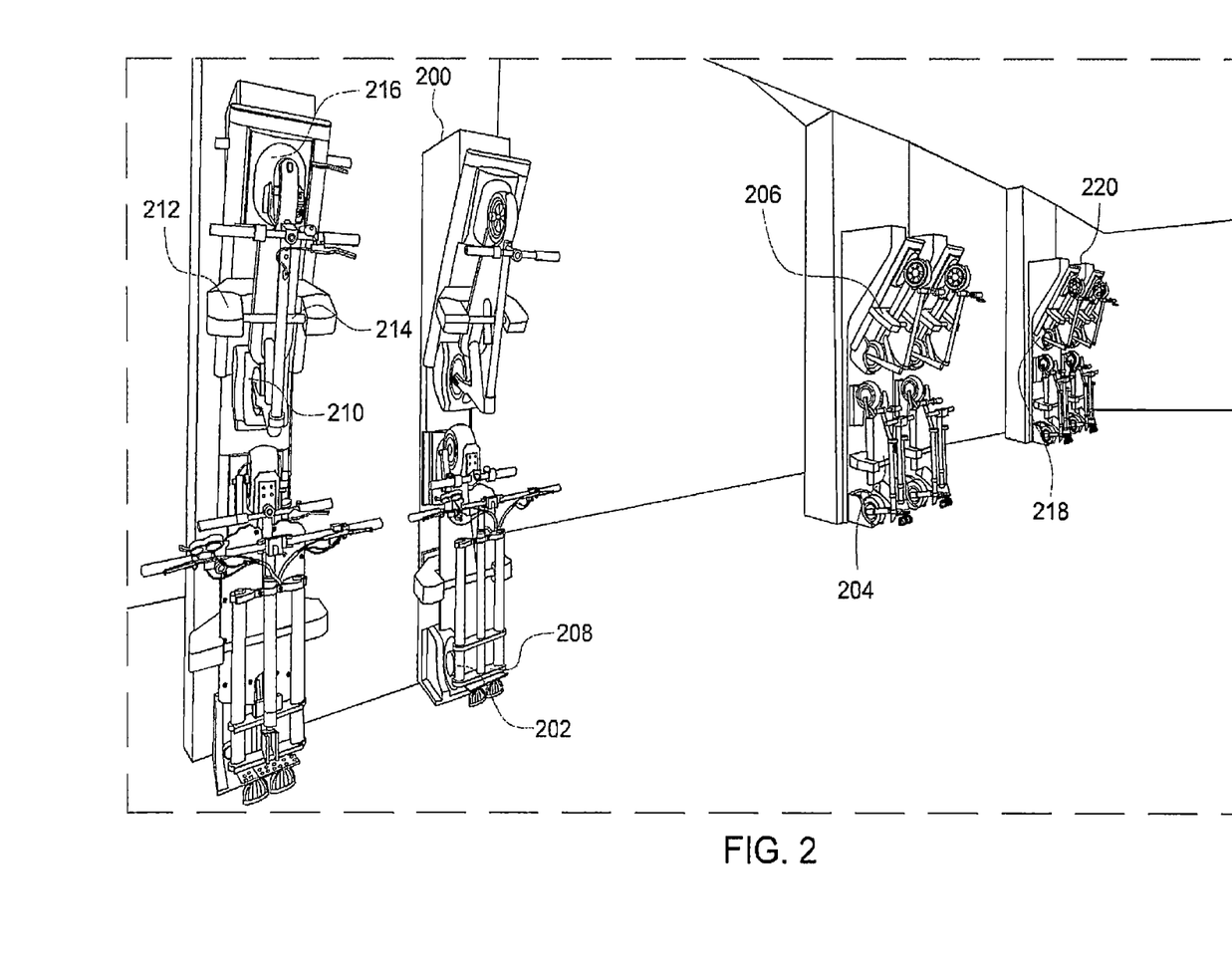
FIG. 2 is an illustrative representation of the universal docking bracket depicting a wall mounted orientation in accordance with an embodiment of the present disclosure.

FIG. 2 is an illustrative representation of a universal docking bracket depicting a wall mounted orientation in accordance with embodiments of the present disclosure. The system provides a charging and docking station 200 for Personal light electric vehicles (PLEVs) 202. The system has two levels of storage space, one lower level port 204 and one upper level port 206. A PLEV is first folded flat 208 before being mounted into the docking station port 200 for storage.

The Personal light electric vehicle (PLEV) has four points of contact with the docking station while it is stored. The first is a cradle 210 that supports the front wheel of the PLEV. The second point of contact is a locking module 212 that grips the center of the PLEV. The locking module has an electronically powered retractable bar 214 that locks the footrest/base of the PLEV against the docking station 200, securing the PLEV in place. The third point of contact is an indent 216 that the rear wheel sits within.

The fourth point of contact is a retractable charging cable that connects to the PLEV and recharges the battery. The lower level of storage space is readily accessible and does not need to be moved for a user to mount a PLEV within it. The upper level of storage can be lowered for a user to gain access to it and mount an PLEV within.

Once the PLEV is mounted on the upper level in its temporarily lowered state, the PLEV can then be raised back to its higher level, reducing the amount of floor space required to store multiple PLEVs. There are several orientations of docking stations that may be deployed depending on the requirements of the environment they are to be installed in. In the embodiment depicted in FIG. 2, it is a wall mounted docking station 218. This orientation typically supports one PLEV on the upper level and one PLEV on the lower level. Multiple docking stations may be mounted side by side along a wall 220.

Figure 3:
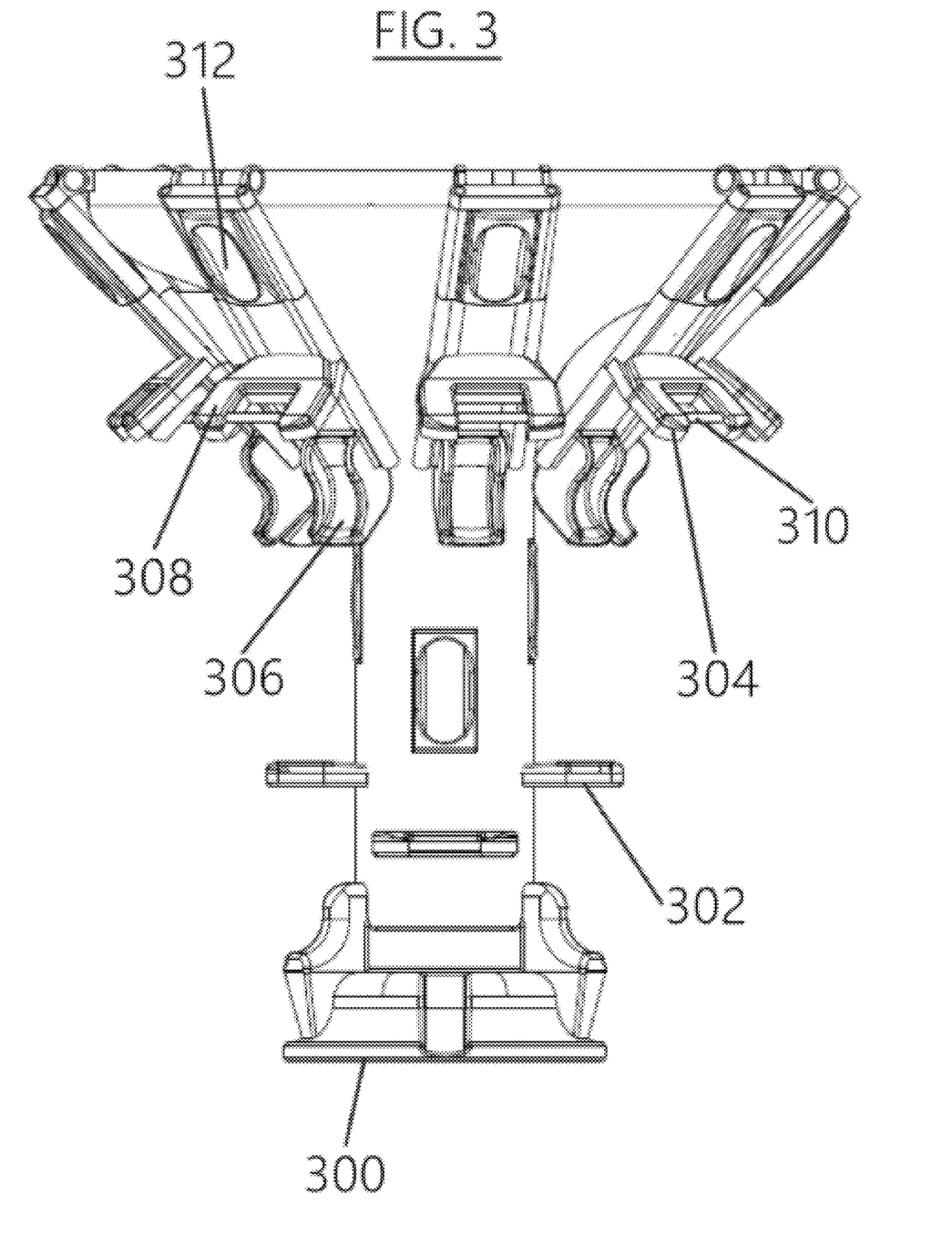
FIG. 3 is an illustrative representation of the universal docking bracket depicting the rotating circular frame orientation in a front view in accordance with an embodiment of the present disclosure.

FIG. 3 is an illustrative representation of a universal docking bracket depicting the rotating circular frame orientation in a front view in accordance with an embodiment of the present disclosure. The system provides a charging and docking station 300 for Personal light electric vehicles (PLEVs). The system has two levels of storage space, one lower level port 302 and one upper level port 304. A PLEV is first folded flat before being mounted into the docking station port for storage.

The PLEV has four points of contact with the docking station while it is stored. The first is a cradle 306 that supports the front wheel of the PLEV. The second is a locking module 308 that grips the center of the Personal light electric vehicles. The locking module has an electronically powered retractable bar 310 that locks the footrest/base of the PLEV against the docking station, securing the PLEV in place. The third point of contact is an indent 312 that the rear wheel sits within. The fourth is a retractable charging cable that connects to the Personal light electric vehicles and recharges the battery.

The lower level of storage space is easily accessible and does not need to move for a user to mount a PLEV within it. The upper level of storage can be lowered for a user to gain access to it and mount a PLEV within. Once the PLEV is mounted within, the temporarily lowered upper level of storage can then be raised back to its higher position, reducing the amount of floor space required to store multiple PLEVs.

There are several orientations of docking stations that may be deployed depending on the requirements of the environment they are to be installed in. In this instance, it is a rotating circular frame that can be attached to the ground or suspended from the ceiling. This may be suitable when the docking station is to be installed in an open space away from a wall. In this orientation the docking typically supports eight PLEVs on the upper level and four PLEVs on the lower level.

Figure 4:
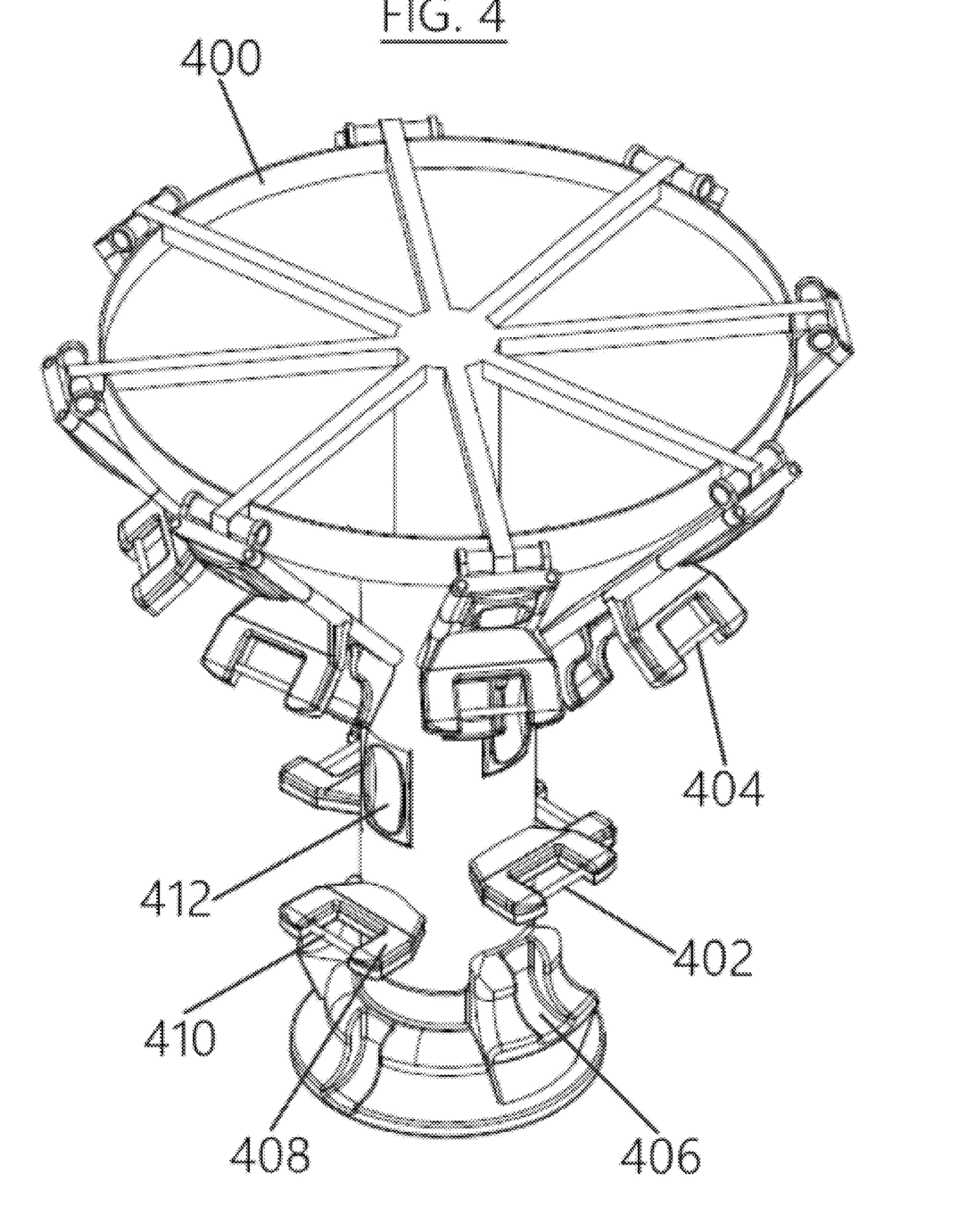
FIG. 4 is an illustrative representation of the universal docking bracket depicting the rotating circular frame orientation in a front/top view in accordance with an embodiment of the present disclosure.

FIG. 4 is an illustrative representation of a universal docking bracket, showing the rotating circular frame orientation, in ISOMETRIC view, in accordance with embodiments of the present disclosure. The bracket comprises a charging and docking station 400 for Personal light electric vehicles (PLEVs). The system has two levels of storage space, one lower level 402 and one upper level 404. A Personal light electric vehicle is first folded flat before being mounted into the docking station for storage.

The Personal light electric vehicle has four points of contact with the docking station while it is stored. The first is a cradle 406 that supports the front wheel of the PLEV. The second is a locking module 408 that grips the center of the Personal light electric vehicle. The locking module has an electronically powered retractable bar 410 that locks the footrest/base of the PLEV against the docking station, securing the PLEV in place. The third point of contact is an indent 412 that the rear wheel sits within. The fourth is a retractable charging cable that connects to the Personal light electric vehicle and recharges the battery.

The lower level of storage space is easily accessible and does not need to move for a user to mount a PLEV within it. The upper level of storage can be lowered for a user to gain access to it and mount a Personal light electric vehicles within. Once the PLEV is mounted within it can then be raised back to a higher position, reducing the amount of floor space required to store multiple PLEVs.

There are several orientations of docking stations that may be deployed depending on the requirements of the environment they are to be installed in. In this instance, it is a rotating circular frame that can be attached to the ground or suspended from the ceiling. This may be suitable when the docking station is to be installed in an open space away from a wall. In this orientation the docking typically supports eight PLEVs on the upper level and four PLEVs on the lower level.

Figure 5:
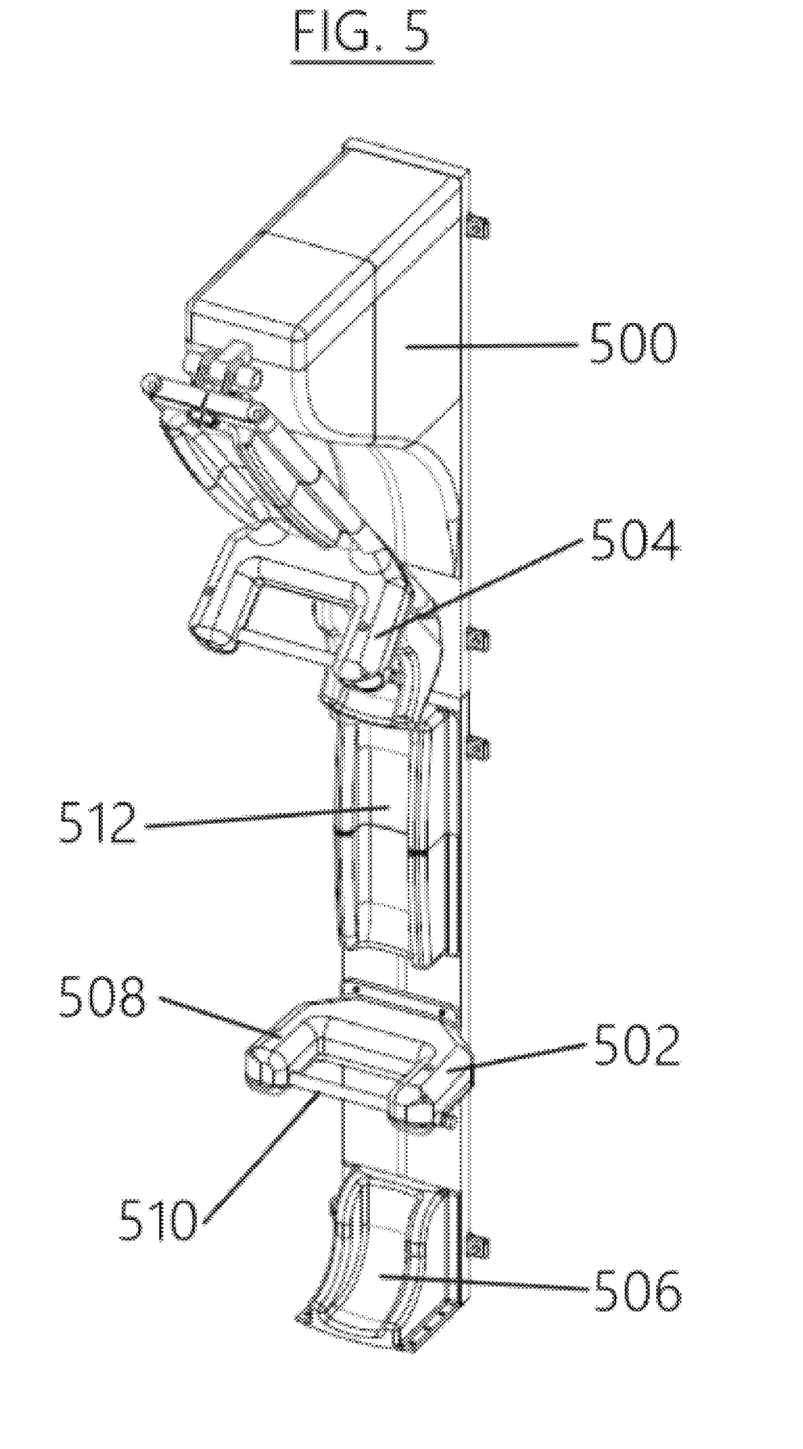
FIG. 5 is an illustrative representation of the universal docking bracket depicting the wall mounted orientation in a side/top view in accordance with an embodiment of the present disclosure.

FIG. 5 is an illustrative representation of a universal docking bracket, showing the wall mounted orientation, in ISOMETRIC view, in accordance with embodiments of the present disclosure. The system as depicted in FIG. 5 is a charging and docking station 500 for Personal light electric vehicles (PLEVs). The system has two levels of storage space, one lower level 502 and one upper level 504. A Personal light electric vehicle is first folded flat before being mounted into the docking station for storage.

The Personal light electric vehicle has four points of contact with the docking station while it is stored. The first is a cradle 506 that supports the front wheel of the PLEV. The second is a locking module 508 that grips the center of the Personal light electric vehicles. The locking module 508 has an electronically powered retractable bar 510 that locks the footrest/base of the PLEV against the docking station, securing the PLEV in place. The third is an indent 512 that the rear wheel sits within. The fourth is a retractable charging cable that connects to the Personal light electric vehicles and recharges the battery.

The lower level of storage space is easily accessible and does not need to move for a user to mount a PLEV within it. The upper level of storage can be lowered for a user to gain access to it and mount a Personal light electric vehicle within. Once the PLEV is mounted within it may then be raised back to a higher position, reducing the amount of floor space required to store multiple PLEVs.

There are several orientations of docking stations that may be deployed depending on the requirements of the environment they are to be installed in. In this instance, it is a wall mounted docking station. This orientation in many embodiments supports one PLEV on the upper level and one PLEV on the lower level. Multiple docking stations may be mounted side by side along a wall.

Figure 6:
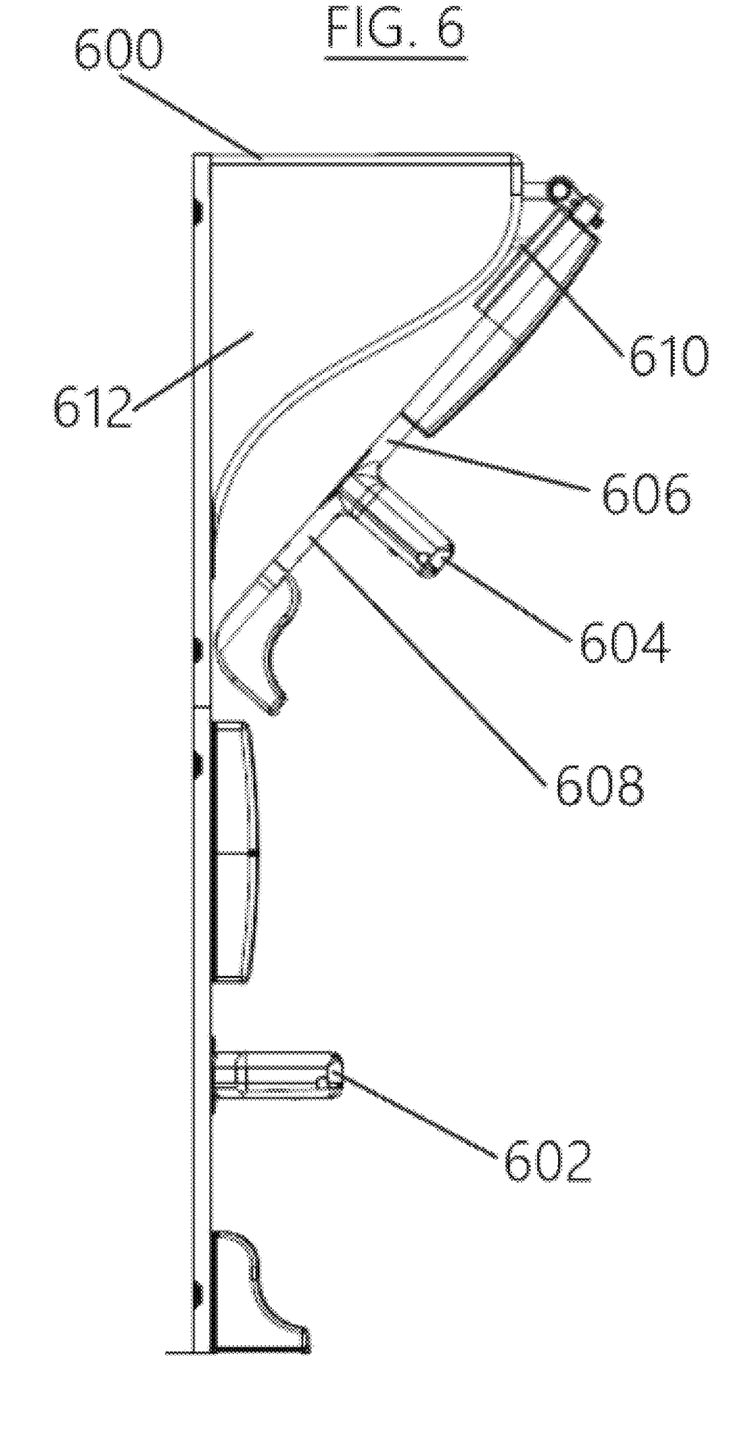
FIG. 6 is an illustrative representation of the universal docking bracket with a Port in a folded/storage position in a side view in accordance with an embodiment of the present disclosure.

FIG. 6 is an illustrative representation of a universal docking bracket, with the Port in a folded/storage position in a side view in accordance with an embodiment of the present disclosure. The embodiment depicted in FIG. 6 is a charging and docking station 600 for Personal light electric vehicles (PLEVs). The system has two levels of storage space, one lower level 602 and one upper level 604.

The upper-level storage port 606 is moved and lowered via electrically powered linear and pneumatic actuators. When in a stored position 608 the port 606 is at an approximate angle of 30 degrees to the vertical. The first step in lowering the port 606 from a stored position to ground level to mount and/or dismount a PLEV is to move the port 606 to a vertical position. This is achieved with a horizontal linear actuator 610 that extends from the casing 612 and rotates the port 606.

The second step is that the port 606 is lowered via telescopic guides and pneumatic actuators. This places the upper-level storage port 606 at ground level for easy access to mount or dismount a PLEV. Once finished the user can then raise the PLEV using the same process in reverse, storing the PLEV in previously unutilized space, increasing the efficiency of the docking station relative to the floor space required.

The system incorporates a retractable universal fast charging cable that protrudes from each of the device's stem ports, at both the lower level and upper level. The system is powered by three phase mains power and is connected to existing smart grid technology.

Figure 7:
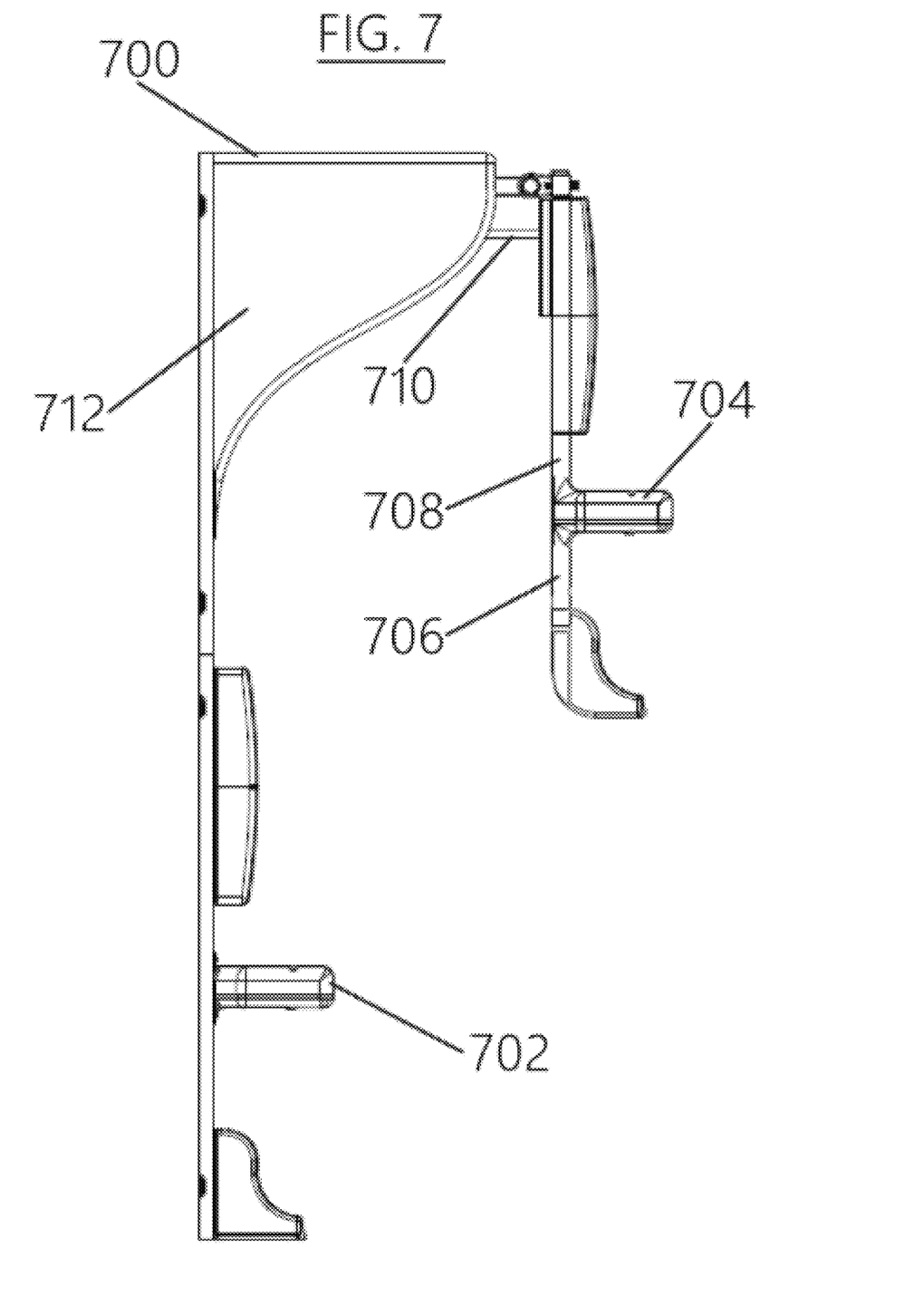
FIG. 7 is an illustrative representation of the universal docking bracket with a Port in vertical position in accordance with an embodiment of the present disclosure.

FIG. 7 is an illustrative representation of a universal docking bracket, with the port in the vertical position in a side view in accordance with embodiments of the present disclosure. The system is a charging and docking station 700 for Personal light electric vehicles (PLEVs). The system has two levels of storage space, one lower level 702 and one upper level 704.

The upper-level storage Port 706 is moved and lowered via electrically powered linear and pneumatic actuators. When in a stored position the port 706 is at an approximate angle of 30 degrees to the vertical. The first step in lowering the port 706 from a stored position to ground level, for mounting or dismounting a PLEV, is to move the port 706 to a vertical position 708. This is achieved with a horizontal linear actuator 710 that extends from the casing 712 and rotates the port 706.

The second step is that the port 706 is lowered via telescopic guides and pneumatic actuators. This places the upper-level storage port 706 at ground level, for easy access to mount or dismount a PLEV. Once finished, the user can then raise the PLEV using the same process in reverse, storing the PLEV in previously unutilized space, which increases the efficiency of the docking station 700 relative to the floor space required.

The docking station 700 incorporates a retractable universal fast charging cable that protrudes from each of the device's stem ports, at both the lower level and upper level. The system is powered by three phase mains power and is connected to existing smart grid technology.

Figure 8:
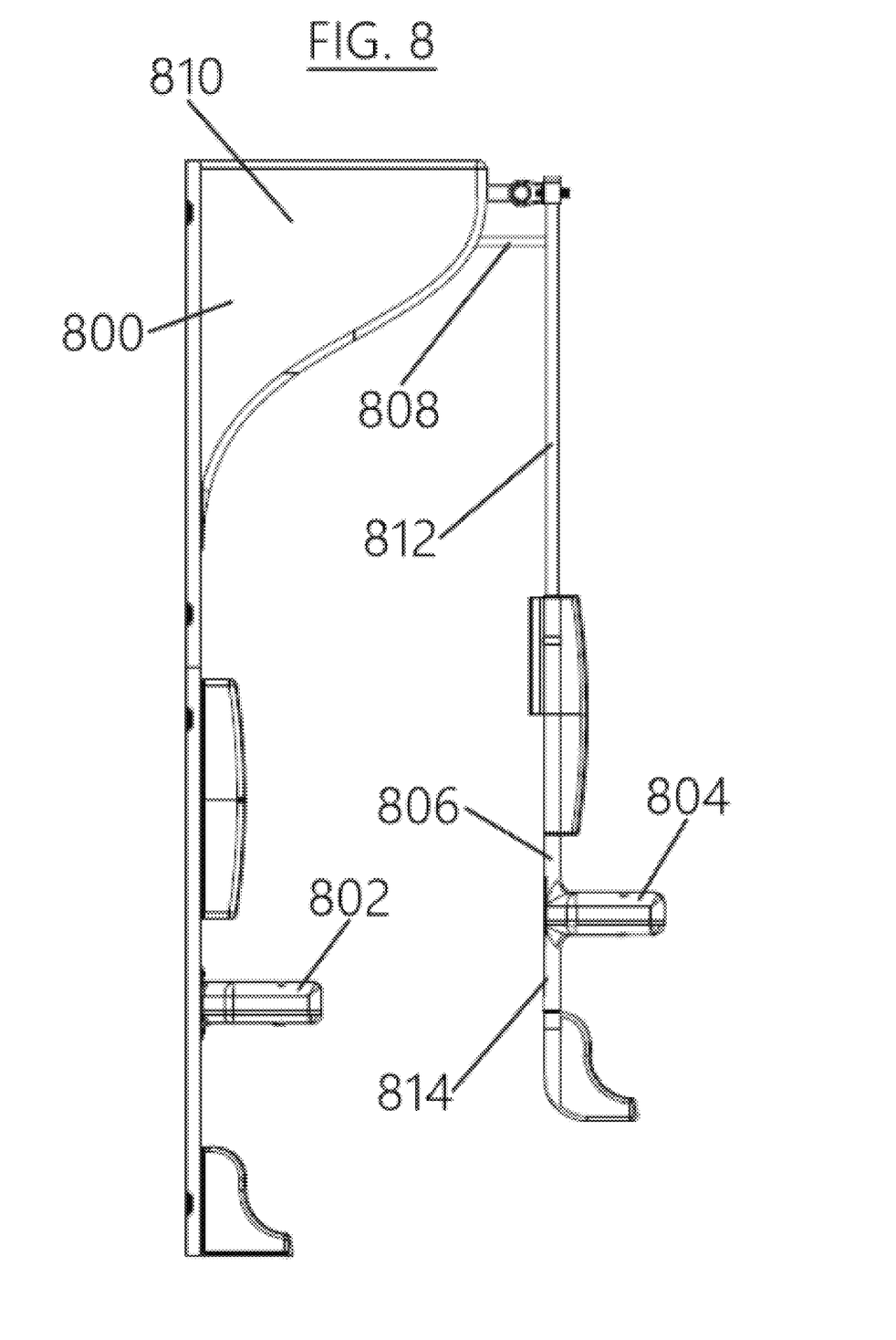
FIG. 8 is an illustrative representation of the universal docking bracket with a Port in a lowered position in a side view in accordance with an embodiment of the present disclosure.

FIG. 8 is an illustrative representation of a universal docking bracket, with the port in the lowered position in a side view in accordance with embodiments of the present system. The embodiment depicted in FIG. 8 is a charging and docking station 800 for Personal light electric vehicles (PLEVs). The station 800 has two levels of storage space, one lower level 802 and one upper level 804.

The upper-level storage Port 806 is moved and lowered via electrically powered linear and pneumatic actuators. When in a stored position the port 806 is at an approximate angle of 30 degrees to the vertical. The first step in lowering the port 806 from a stored position to ground level, for mounting or dismounting a PLEV, is to move the port 806 to a vertical position. This is achieved with a horizontal linear actuator 808 that extends from the casing 810 and rotates the port 806.

The second step is that the port 806 is lowered via telescopic guides and pneumatic actuators 812. This places the port 806 at ground level 814 for easy access to mount or dismount a PLEV. Once finished the user can then raise the PLEV using the same process in reverse, storing the PLEV in previously unutilized space, increasing the efficiency of the docking station relative to the floor space required.

The system incorporates a retractable universal fast charging cable that protrudes from each of the device's stem ports, at both the lower level and upper level. The system is powered by three phase mains power and is connected to existing smart grid technology.

Figure 9:
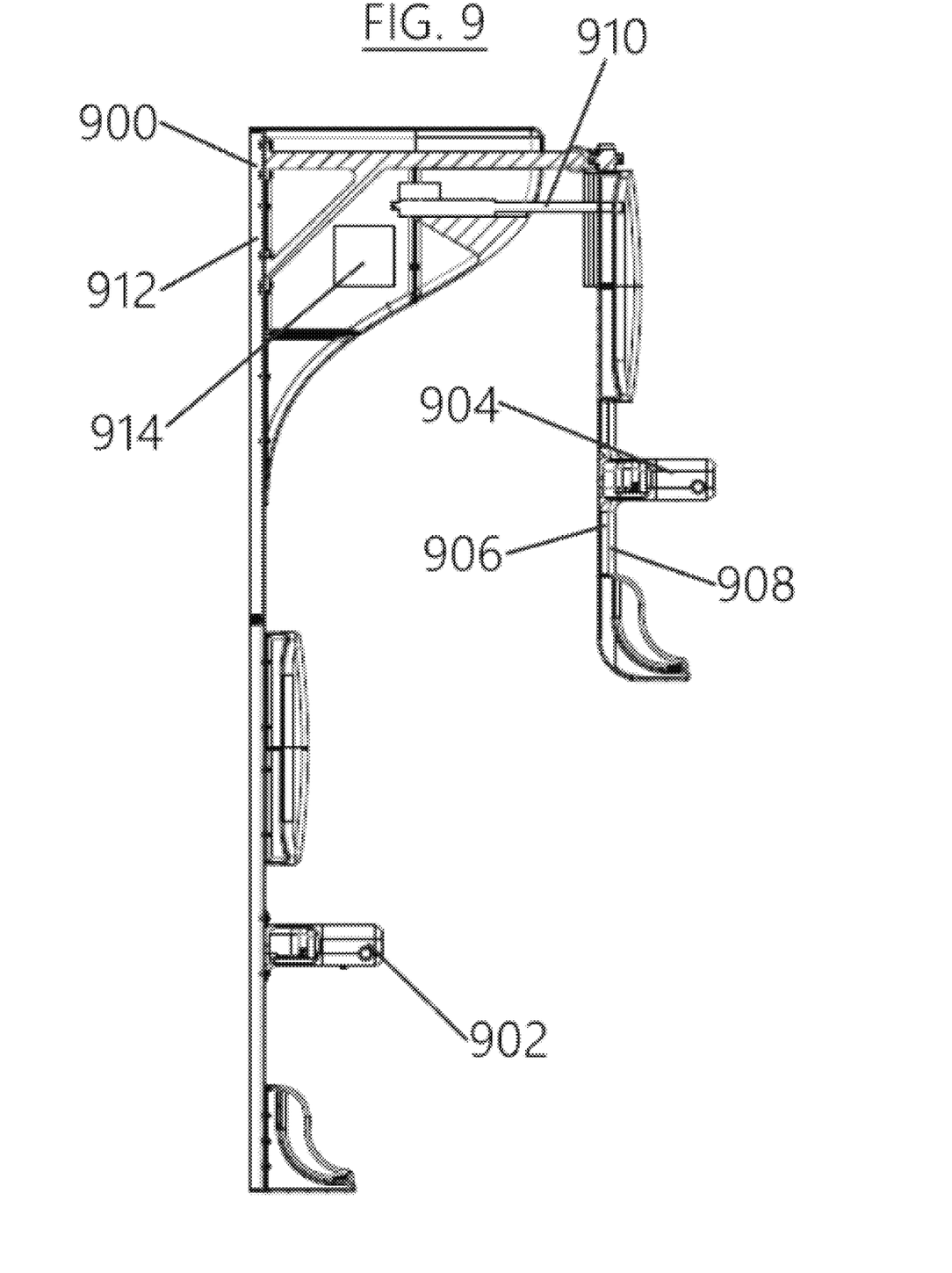
FIG. 9 is an illustrative representation of the universal docking bracket in a sectional view depicting internal components in accordance with an embodiment of the present disclosure.

FIG. 9 is an illustrative representation of a universal docking bracket in a section view that depicts internal components in accordance with embodiments of the present system. The embodiment depicted in FIG. 9 is a charging and docking station 900 for Personal light electric vehicles (PLEVs). The system has two levels of storage space, one lower level 902 and one upper level 904.

The upper-level storage port 906 is moved and lowered via electrically powered linear and pneumatic actuators. When in a stored position the port 906 is at an approximate angle of 30 degrees to the vertical. The first step in lowering the port 906 from a stored position to ground level, for mounting or dismounting a PLEV, is to move the port 906 to a vertical position 908. This is achieved with a horizontal linear actuator 910 that extends from the casing 912 and rotates the port 906.

The second step is that the port 906 is lowered via telescopic guides and pneumatic actuators. This places the port 906 at ground level for easy access to mount or dismount a PLEV. Once finished the user can then raise the PLEV using the same process in reverse, storing the PLEV in previously unutilized space, increasing the efficiency of the docking station 900 relative to floor space required.

The system incorporates a retractable universal fast charging cable that protrudes from each of the device's stem ports, at both the lower level and upper level. The system is powered by three phase mains power and is connected to existing smart grid technology. The electrical components are inside the casing 914.

Figure 10:
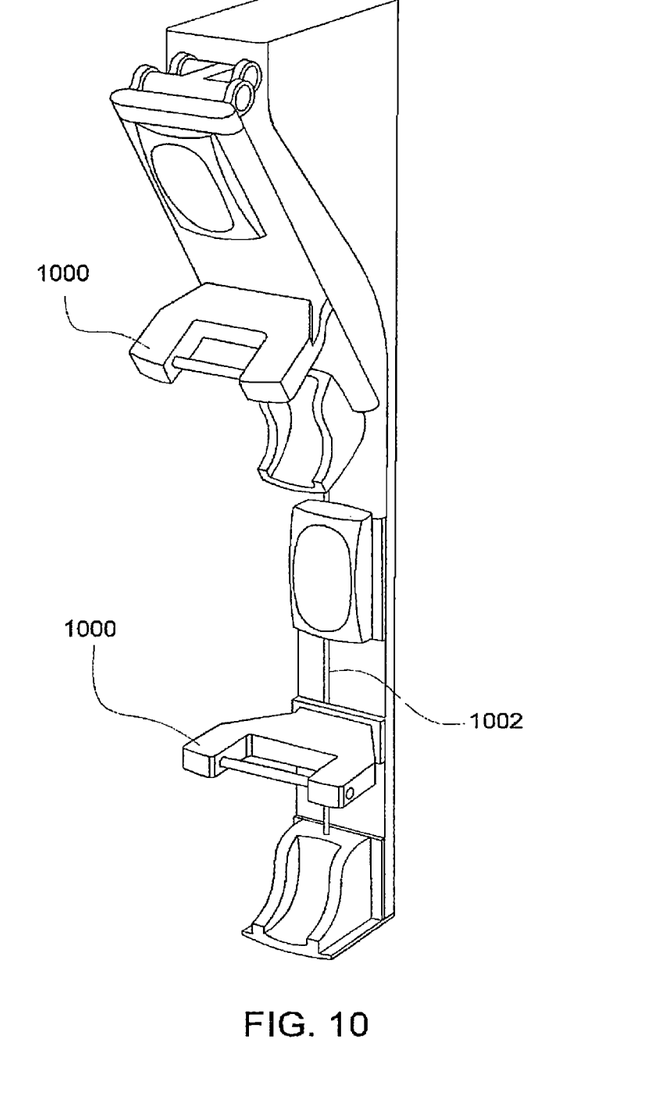
FIG. 10 is an illustrative representation of the universal docking bracket depicting retractable charging cable and UVED light strip in accordance with an embodiment of the present disclosure.

FIG. 10 is an illustrative representation of a universal docking bracket, showing the retractable charging cable and UVED light strip, in accordance with embodiments of the present system. The system is a charging and docking station for Personal light electric vehicles (PLEVs). The system has two levels of storage space, one lower level and one upper level.

The system incorporates a retractable universal fast charging cable that protrudes from each of the device's stem ports, at both the lower level and upper level. The retractable cable port is built into the side of the locking case 1000. A light strip 1002 is built into the charging and docking station and is installed vertically from the base to the top. It contains UVEDs (Ultraviolet Emitting Diodes) which operate at 400-500 nm wavelengths. The Ultraviolet light kills germs and sterilizes Personal light electric vehicles mounted within.

The system may have two vertical levels of storage, three levels, four levels, or any other variations known in the art. The system may support Personal light electric vehicles, electric bicycles, electric hoverboards, combinations of electric vehicles, and other variations known in the art.

The upper-level port may support one electric vehicle, two electric vehicles, four electric vehicles, and other variations known in the art. The system may support single vehicle docking and locking, dual vehicle docking and locking, multi-vehicle docking and locking, and other variations known in the art.

The system may be formed of stainless polyurethane, polycarbonate, stainless steel, aluminum, glass, ceramic, carbon fiber, and other variations known in the art. The manufacturing method may make use of injection molding, rotational molding, compression molding, die casting, laser cutting, 3D printing, and other variations known in the art.

The system may be on wheels or sliders so that it can be moved around in its environment. The wheels can lock for security and safety. The system incorporates computer software programming to schedule storage and charging access via internet-based web application or native device application interface and comprising a digital database ledger.

In an embodiment, a universal docking bracket system for vehicles is provided. The system comprises a two-level charging and docking station comprising an upper-level port and a lower-level port. Each port comprises a cradle that supports a front wheel of a two-wheeled vehicle, a locking module that grips a center of the vehicle, and an indentation for placement of a rear wheel of the vehicle. The vehicle is a plug-in Personal light electric vehicle comprising an electric scooter. The vehicle is folded flat prior to docking by the system. Each port further comprises a retractable charging cable that connects to the vehicle and recharges a battery in the vehicle. The vehicle while docked and receiving charging is positioned vertically and in an upside-down manner on either port. The locking module has an electronically powered retractable bar that locks a footrest/base of the vehicle against the port. The upper-level port is lowered from its stationary position, promoting ease in attaching and detaching the vehicle. Upon at least one of releasing a vehicle and receiving attachment of a vehicle, the upper-level port is raised to its stationary position above the lower-level port. Multiple upper-level ports and lower-level ports are attached to a singular rotating circular bracket frame and to a ground surface.

In another embodiment, a docking system for plug-in electric vehicles is provided comprising an upper port and a lower port, each port securing an electric vehicle held vertically. The upper port is secured at an angle of 30 degrees to vertical when in stored position that receives movement from the angled position to a vertical position, receives lowering to ground level via telescopic guides and via pneumatic actuators, at least one of releases a first electric vehicle and receives attachment of a second electric vehicle and receives raising to a level of a stored position above the upper port and receives securing at an angle of 30 degrees. Each of the upper port and the lower port further comprises, a cradle that supports a front wheel of the vehicle, wherein the vehicle is two-wheeled, a locking module that grips a center of the vehicle, and an indentation for placement of a rear wheel of the vehicle. The vehicle while in stored position attached to either port is positioned vertically and in an upside-down manner. The locking module has an electronically powered retractable bar that locks a footrest/base of the vehicle against the port. The upper port receives movement from the angled position to the vertical position via use of a horizontal linear actuator that extends from casing and rotates the upper port.

In yet another embodiment, a docking and charging bracket system for plug-in Personal light electric vehicles (PLEV) is provided. The system comprises a multi-level structure for securing PLEVs, one bracket at each level, each bracket securely holding one PLEV and a light strip containing ultraviolet emitting diodes (UVED) that receives activation, emits ultraviolet light at 400-500 nm wavelengths, directs the ultraviolet light at the PLEVs, and kills germs and sterilizes surfaces of the PLEVs. The light strip is installed vertically from a base of the structure to a top of the structure. Each bracket further comprises a cradle that supports a front wheel of the PLEV, wherein the PLEV is two-wheeled, a locking module that grips a center of the PLEV, and an indentation for placement of a rear wheel of the PLEV. The system incorporates computer software programming to schedule storage and charging access via internet-based web application or native device application interface and comprising a digital database ledger.

What is claimed is:

1. A universal docking bracket system for vehicles, comprising:
   one or more two-level charging and docking stations, each comprising an upper-level port and a lower-level port, each port of each docking station comprising each of the following components:
   a cradle that supports a front wheel of a two-wheeled vehicle;
   a locking module that grips a center of said vehicle; and an indentation for placement of a rear wheel of said vehicle;
   wherein the locking module has an electronically powered retractable bar that locks a footrest/base of said vehicle against the port;
   wherein the cradle, locking module, and indentation of each port form three separate points of contact for supporting said vehicle;
   and
   wherein the ports are configured such that a two-wheeled vehicle in a stored position in an upper-level port of a given changing and docking station is suspended by the three points of contact above the lower-level port of said charging and docking station.

2. The system of claim 1, wherein the vehicle is a plug-in Personal light electric vehicle.

3. The system of claim 1, wherein the vehicle is folded flat prior to docking by the system.

4. The system of claim 1, wherein each port further comprises a retractable charging cable that connects to the vehicle and recharges a battery in the vehicle.

5. The system of claim 1, wherein the vehicle while docked and receiving charging is positioned vertically and in an upside-down manner on either port.

6. The system of claim 1, wherein the upper-level port is lowered from its stationary position, promoting ease in attaching and detaching the vehicle.

7. The system of claim 6, wherein upon at least one of releasing a vehicle and receiving attachment of a vehicle, the upper-level port is raised to its stationary position above the lower level Port.

8. The system of claim 1, wherein multiple upper-level ports and lower-level ports are attached to a singular rotating circular bracket frame and to a ground surface.

9. A docking system for plug-in electric vehicles, comprising:
   an upper port and a lower port, each port securing an electric vehicle held vertically, the upper port secured at an angle of 30 degrees to vertical when in stored position that:
   receives movement from the angled position to a vertical position,
   receives lowering to ground level via telescopic guides and via pneumatic actuators,
   at least one of releases a first electric vehicle and receives attachment of a second electric vehicle, and
   receives raising to a level of a stored position above the upper port and receives securing at an angle of 30 degrees and
   wherein each port further comprises a locking module that has an electronically powered retractable bar that locks a footrest/base of the vehicle against the port;
   wherein a cradle, the locking module, and an indentation of each port form three separate points of contact for supporting each stored vehicle;
   wherein the upper port is configured such that a vehicle in a stored position in the upper port is suspended by the three points of contact above the lower port.

10. The system of claim 9, wherein each of the upper port and the lower port further comprises: a cradle that supports a front wheel of the vehicle, wherein the vehicle is two-wheeled, a locking module that grips a center of the vehicle; and an indentation for placement of a rear wheel of the vehicle.

11. The system of claim 9, wherein the vehicle while in stored position attached to either port is positioned vertically and in an upside-down manner.

12. The system of claim 9, wherein the upper port receives movement from the angled position to the vertical position via use of a horizontal linear actuator that extends from casing and rotates the upper port.

* * * * *